(12) United States Patent
Huber et al.

(10) Patent No.: US 6,687,428 B2
(45) Date of Patent: Feb. 3, 2004

(54) OPTICAL SWITCH

(75) Inventors: Avigdor Huber, Yehud (IL); Assaf Nahum, Gedera (IL); Atzmon Ofri, Kiriat Ekron (IL); Michael M. Tilleman, Kfar Sava (IL); Idan Paiss, Tel Aviv (IL); Richard Tasgal, Tel Aviv (IL); Galia Goldner, Tel Aviv (IL); William A. Bodkin, Needham, MA (US)

(73) Assignee: Tera Op (USA) Inc., Wilmington, DE (US)

( * ) Notice: Subject to any disclaimer, the term of this patent is extended or adjusted under 35 U.S.C. 154(b) by 184 days.

(21) Appl. No.: 09/948,143

(22) Filed: Sep. 6, 2001

(65) Prior Publication Data

US 2002/0067880 A1 Jun. 6, 2002

Related U.S. Application Data

(60) Provisional application No. 60/230,694, filed on Sep. 7, 2000.

(51) Int. Cl.[7] ................................................ G02B 6/26
(52) U.S. Cl. ............................ 385/17; 385/18; 385/19; 385/20
(58) Field of Search .............................. 385/17, 18, 19, 385/20, 21–24, 16; 359/856, 857, 858, 859

(56) References Cited

U.S. PATENT DOCUMENTS

| | | | |
|---|---|---|---|
| 4,933,944 A | 6/1990 | McGraw | 372/18 |
| 4,935,931 A | 6/1990 | McGraw | 372/18 |
| 5,070,260 A | 12/1991 | Wong | 359/330 |
| 5,177,633 A | 1/1993 | Wong | 359/330 |
| 5,408,556 A | 4/1995 | Wong | |
| 5,457,556 A | 10/1995 | Shiragaki | |
| 5,715,337 A | 2/1998 | Spitzer et al. | |
| 5,872,880 A | 2/1999 | Maynard | |
| 5,937,117 A | 8/1999 | Ishida et al. | |
| 6,038,058 A | 3/2000 | Robinson et al. | 359/293 |
| 6,075,239 A | 6/2000 | Aksyuk et al. | |
| 6,088,145 A | 7/2000 | Dickensheets et al. | |
| 6,097,859 A | 8/2000 | Solgaard et al. | |

(List continued on next page.)

OTHER PUBLICATIONS

Press Release: OMM MEMS–based Optical Switches Pass Rigorous Telcordia Requirements. www.omminc.com (Jul. 16, 2001).

Press Release: A World's First for Optical Switching: Live Data Traffic Switched by MEMS–bsaed Optical Switch Subsystems Delivered by OMM Inc. www.omminc.com (Mar. 26, 2000).

Press Release: Optical switches delivered by Optical Micro Machines Inc. (OMM) at the core of Siemens' TransxpressTM optical service node. Siemens demonstrates optical switching at CeBIT 2000 using optical switching subsystems from OMM Inc. www.omminc.com (Mar. 7, 2000).

(List continued on next page.)

*Primary Examiner*—Mohammad Sikder
(74) *Attorney, Agent, or Firm*—Mark M. Friedman

(57) ABSTRACT

A spatial light modulator (SLM) has electrically controllable microelectromechanical reflectors arranged in a chain-like manner along an axis such that an optical beam propagates by reflection from an input down the chain to an output. Each reflector can be moved to a selected one of a number of discrete switching positions. The position determines the angle at which the beam is reflected toward the next reflector in the chain. The combination of positions in which the reflectors are oriented is determinative of the angle at which the signal exits the output. The SLM can be included in a switch. An SLM in the input section of the switch can be adjusted to direct the beam such that it impinges upon a selected switch output. Multiple SLMs can be included in an array to provide a cross-connect or crossbar switch.

48 Claims, 8 Drawing Sheets

U.S. PATENT DOCUMENTS

| | | | |
|---|---|---|---|
| 6,154,587 | A | 11/2000 | Okayama |
| 6,198,565 | B1 | 3/2001 | Iseki et al. ............... 359/224 |
| 6,205,267 | B1 | 3/2001 | Aksyuk et al. |
| 6,222,954 | B1 | 4/2001 | Riza |
| 6,259,835 | B1 | 7/2001 | Jing |
| 6,288,807 | B1 | 9/2001 | Wu et al. |
| 6,317,529 | B1 | 11/2001 | Kashima |
| 6,430,328 | B1 * | 8/2002 | Culver et al. ............. 385/16 |
| 6,587,611 | B1 * | 7/2003 | Hunt ....................... 385/18 |
| 2001/0008457 | A1 | 7/2001 | Zhang |

OTHER PUBLICATIONS

Press Release: Revolutionary MEMS Optical Switch Slated to Become the Heart of Optical Communications Systems. www.omminc.com (Dec. 9, 1999).

Press Release: OMM Focuses Market Position on Mid–sized MEMS Photonic Switch Modules and Subsystems. www.omminc.com (Jul. 27, 2001).

website: www.omminc.com, discovered on Aug. 8, 2001, however available maybe as early as Feb. 2000.

* cited by examiner

OPTICAL SWITCH

CROSS-REFERENCE TO RELATED APPLICATION

The benefit of the filing date of U.S. Provisional Patent Application Ser. No. 60/230,694, filed Sep. 7, 2000, entitled "ARCHITECTURE OF OPTICAL SWITCH USING MEMBRANE LIKE MIRROR," is hereby claimed, and the specification thereof incorporated herein in its entirety.

BACKGROUND OF THE INVENTION

1. Field of the Invention

The present invention relates generally to optical switches and, more specifically, to an optical switch having an array of movable microelectromechanical reflectors.

2. Description of the Related Art

To achieve high data rates, optical switches are used in many conventional optical fiber communication networks. An optical switch can have a crossbar configuration, in which any selected one of a bundle of input fibers can be coupled to any selected one of a bundle of output fibers.

In some optical switches, the fibers themselves are mechanically moved to switch the optical path between input and output fibers. Such switches suffer from precision and repeatability alignment problems. Slight misalignment between the selected input and output fibers can cause unacceptable signal power loss at the interface. The mechanisms that are required are complex, uneconomical and have slow switching speeds, thereby limiting their use in commercial communications networks.

In other optical switches, one or more mirrors or reflectors are moved to switch the optical path between input and output fibers. Actively controlled mirrors can be fabricated using microelectromechanical systems (MEMS) technology. MEMS technology promises to offer low cost, compact optical modules through the use of low-cost cost batch fabrication. The key mechanical components of MEMS-based micro-machined mirrors can be fabricated on silicon chips using well established, very-large-scale integration (VSLI) complementary metal-oxide semiconductor (CMOS) foundry processes. These processes can include photolithography, material deposition, and chemical etching.

While the operating principles of MEMS optical switching devices may appear to be simple, problems exist with conventional MEMS optical switching devices because of the need for precision control of a movable optical element in a high-speed environment. Conventional MEMS optical switching devices lack precise and controlled mirror movement mechanisms. A movable optical element such as a mirror is disclosed in copending U.S. patent application Ser. No. 09/862,958, filed May 22, 2001, entitled "Method and System for Ultra-Fast Switching of Optical Signals," assigned to the assignee of the present invention and incorporated herein by this reference in its entirety. One advantage of the disclosed optical element is that it can be very precisely positioned. For example, a mirror can be made to move to one of two precisely defined positions in response to an electrical control signal.

It would be desirable to provide a MEMS-based optical switch having precisely controllable reflectors. The present invention addresses this problem and others in the manner described below.

SUMMARY OF THE INVENTION

The present invention relates to a spatial light modulator (SLM) that, in one aspect, has electrically controllable microelectromechanical reflectors arranged in a chain-like manner along an axis such that an optical signal propagates by reflection from an input down the chain to an output. A selected reflector can be moved to a selected one of a number of discrete switching positions. The position determines the angle at which the signal is reflected toward the next reflector in the chain. The combination of positions in which the reflectors are oriented is determinative of the angle at which the signal exits the output. In an illustrative embodiment of the invention, reflectors can move about more than one axis. In such an embodiment, the combination of positions in which the reflectors are oriented is determinative of a two-dimensional direction at which the signal exits the output. Thus, the output signal can be directed at a target point in space.

In the illustrated embodiment of the invention, an optical switch includes an output section comprising a number of SLMs with their inputs arranged in an array or other two-dimensional arrangement. Thus, the input of any of the SLMs of the output section can receive an optical signal. Such an optical switch can also include an input section comprising one or more of the same or similar type of SLM. The outputs of the SLMs of the input section of the switch are arranged to optically couple with the inputs of the SLMs of the output section of the switch. Thus, an SLM of the input section can direct a signal in two-dimensional space such that it impinges upon a selected one of the inputs of the SLMs of the output section. In other words, any of the SLMs of the input section can selectably direct a signal to one of the SLMs of the output section. The switch thus optically couples any selected one of the inputs to any selected one of the outputs in a cross-connect or crossbar manner. Any suitable optical elements, such as lenses, mirrors, and the like, can be interposed between the input and output sections to facilitate mechanical construction or for other purposes.

It is to be understood that both the foregoing general description and the following detailed description are exemplary and explanatory only and are not restrictive of the invention, as claimed.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment, and wherein.

DETAILED DESCRIPTION

Figure 1:
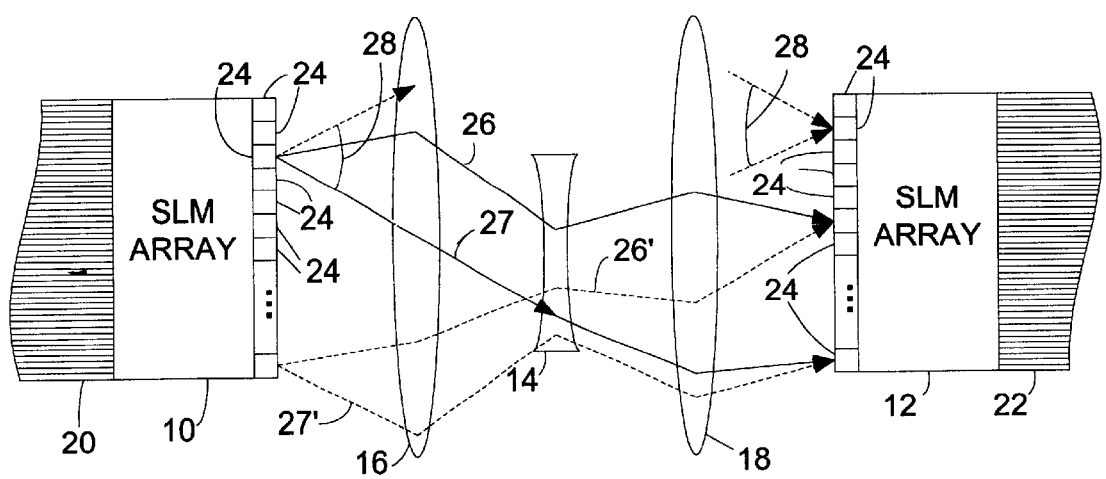
FIG. 1 illustrates an embodiment of an optical switch having input and output sections, each with a spatial light modulator (SLM) array.

As illustrated in FIG. 1, a switch includes a first spatial light modulator (SLM) array 10 and a second SLM array 12 with an optical pathway between them that includes a negative lens 14 and two positive lenses 16 and 18. As described below in further detail, SLM arrays 10 and 12 each include any suitable number of SLMs. Each SLM is associated with a first port that is connectable to one fiber of a bundle of optical fibers 20 and 22. Each SLM is also associated with an aperture-like second port 24 through which it can transmit or receive optical signal, such as light beams 26, 26', 27 and 27', at a selected angle. The angle is selected by applying electrical control signals (not shown) as described below. A selected SLM of array 10 can, for example, receive an optical signal from the fiber to which it is connected and transmit or direct beam 26 at any of a number of discrete, selected angles within an angle range 28.

The optical pathway, which can include any suitable elements, such as lenses 14, 16 and 18, in any suitable arrangement, couples beam 26 between SLM array 10 and SLM array 12. It should be appreciated, as explained in further detail below, that beam 26 inherently has a Gaussian shape and is not in actuality the same as the single ray or line representing it in FIG. 1 and other drawing figures. Thus, the optical pathway coupling SLM arrays 10 and 12 is designed to focus beam 26 to minimize insertion losses.

The optical pathway is arranged such that beam 26 emanating from a port 24 of SLM array 10 at the selected angle is directed to impinge upon only one port 24 of SLM array 12. By selecting a different angle, beam 26 can be made to impinge upon a different port 24 of SLM array 12.

Each of the discrete, selectable angles within range 28 corresponds to a different one of ports 24 of SLM array 12. Thus, selecting the angle at which beam 26 emanates from one of ports 24 of SLM array 10 selects the one of ports 24 of SLM array 12 upon which beam 26 impinges.

The optical pathway is arranged such that a beam 26 emanating from a port 24 of SLM array 10 at a given angle impinges upon the same port 24 of SLM array 12 as any other beam 26' emanating from another port 24 at that same angle. Thus, for example, because beams 26 and 26' are parallel (i.e., emanate at the same angle as each other) where they emanate from their respective ports 24 of SLM array 10, beam 26 impinges upon the same port 24 of SLM array 12 as beam 26'. Likewise, because beams 27 and 27' are parallel (i.e., emanate at the same angle as each other) where they emanate from their respective ports 24 of SLM array 10, beam 27 impinges upon the same port 24 of SLM array 12 as beam 27'. Note that the beam angle at its source port 24 of SLM array 10 uniquely corresponds to a destination port 24 of SLM array 12. A set of predetermined, discrete angles can be selected, each having a corresponding destination port 24 of SLM array 12. Stated another way, each angle uniquely represents a destination address or, in a communications switch, a channel.

Figure 2:
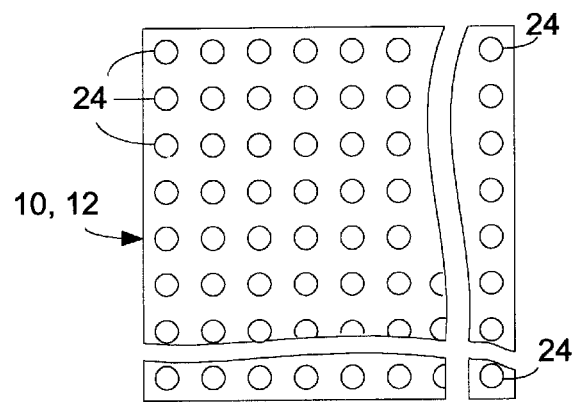
FIG. 2 illustrates an end view of an SLM array.

The angles at which beam 26 can emanate from array 10 and impinge upon array 12 can be in two-space. In other words, angle range 28 can be a solid angle range; array 10 can direct beam 26 at any point in space within range 28. Accordingly, ports 24 can be disposed in a suitable two-dimensional arrangement, such as the rectangular array illustrated in FIG. 2. In the illustrated embodiment, each of SLM arrays 10 and 12 has 256 ports 24 and thus 256 corresponding SLMs. Nevertheless, in other embodiments an SLM array can have any other suitable number of ports 24 (and corresponding SLMs) arranged in any suitable pattern or other arrangement.

Optical beam 26 can be of any suitable type and any suitable electromagnetic frequency, such as visible or infrared. The switch can be used as a switch in communications routers, as a cross-connect switch, and in any other system in which each of a plurality of optical inputs is to be coupled to any selected one of a plurality of optical outputs in a crossbar fashion.

Figure 3A:
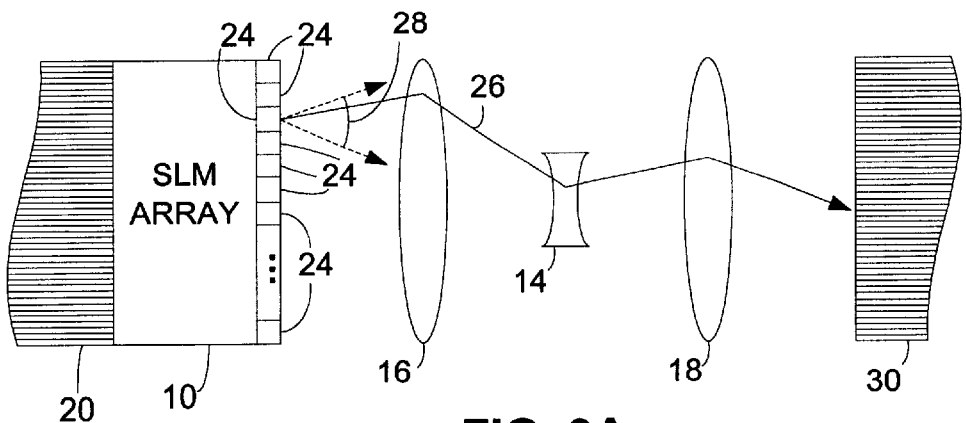
FIG. 3A illustrates an alternative embodiment of the switch having an SLM array in the input section receiving input signals from optical fibers and a bundle of multi-mode optical fibers in the output section.

As illustrated in FIG. 3A, rather than each of the two sections of the switch having one SLM array 10 or 12, an alternative switch arrangement can have a first section with SLM array 10 and a second section with only a fiber bundle 30. This switch can be operable the alignment of each fiber of bundle 30 with the remainder of the apparatus is such that at a beam emanating from SLM array 10 at any angle within range 28 is incident and focused upon the fiber core. Because multi-mode fibers have wide angles of acceptance and large cores, it is contemplated that multi-mode fibers rather than single-mode fibers be used in such an embodiment of the invention. Nevertheless, various types of fibers may be suitable. This embodiment may be more economical than that shown in FIG. 1 because only one SLM array 10 is included rather than two. Nevertheless, the switch illustrated in FIG. 1 can be useful if, for example, the fibers of bundle 22 do not have a sufficiently great angle of acceptance to directly accept the beam (i.e., without the aid of SLM 12), such as is true of most single-mode fibers. In that case, the SLM of array 12 to which beam 26 is directed is adjusted to have the acceptance angle necessary to receive beam 26 and channel it to the corresponding fiber of bundle 22.

Figure 3B:
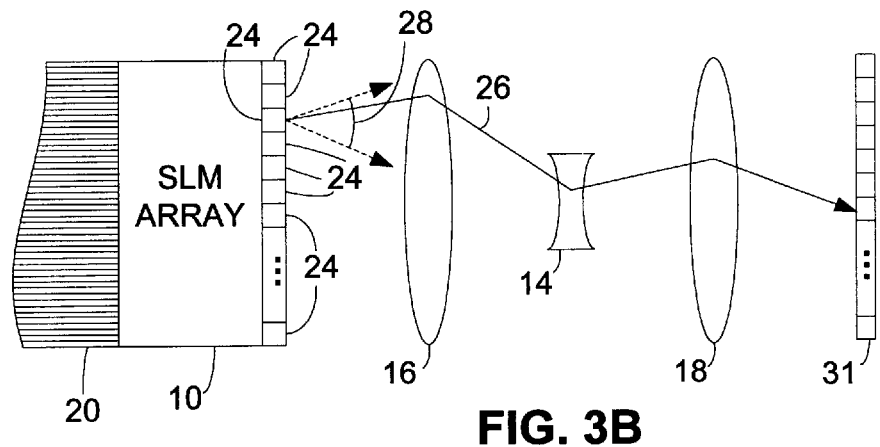
FIG. 3B illustrates another alternative embodiment of the switch having an SLM array in the input section receiving input signals from optical fibers and a detector array in the output section.

As illustrated in FIG. 3B, another alternative embodiment of a switch can have a first section similar to that described above with regard to FIGS. 1 and 3A but a second section with an photodetector array 31. Like each of the fibers in bundle 30 in the above-described embodiment, each detector in array 31 can receive beam 26, thereby defining the output of the switch.

The two switch embodiments described above with regard to FIGS. 3A and 3B illustrate that the output section can comprise various types of elements and is not limited to an SLM array. The input section can comprise various elements as well. As illustrated in FIG. 3B, still another alternative embodiment of a switch can have a first section in which the inputs to the switch are lasers 33 rather than fibers 20. A laser 33 can be any suitable type of laser source (i.e., source of coherent optical signals), including not only tube-based lasers but also light-emitting diode lasers (commonly referred to as "laser diodes") and other known types. These exemplary switch embodiments will likely cause persons skilled in the art to which the invention relates to consider still other switch embodiments comprising various other combinations of elements in the input and output sections of the switch.

Figure 3C:
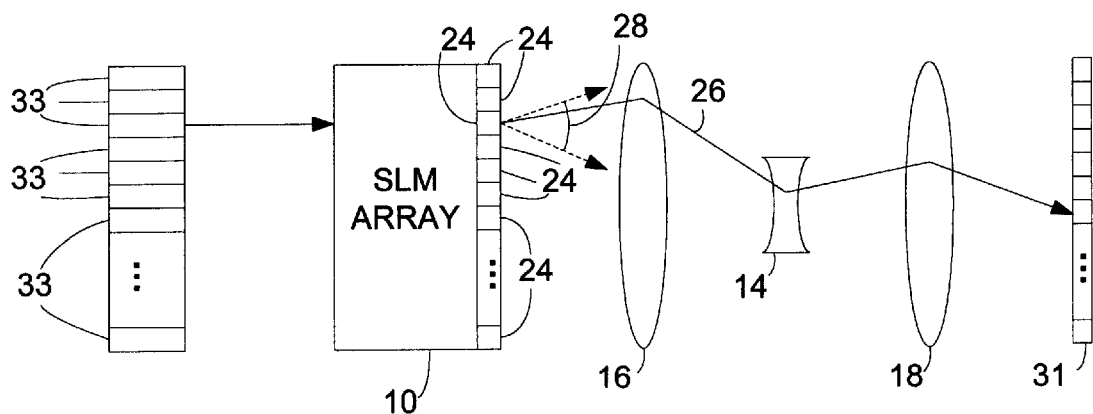
FIG. 3C illustrates still another alternative embodiment of the switch having an SLM array in the input section receiving input signals from lasers and a detector array in the output section.

Note that, as described above, in any of the embodiments illustrated in FIGS. 3A, 3B and 3C, a beam 26 emanating from an SLM of array 10 at a given angle impinges upon the same SLM of array 12 as any other beam 26 emanating from an SLM of array 10 at that angle. In other words, the property described above, whereby the beam angle uniquely corresponds to a destination address or channel, holds true regardless of the manner in which the switch of the present invention is embodied.

Figure 4:
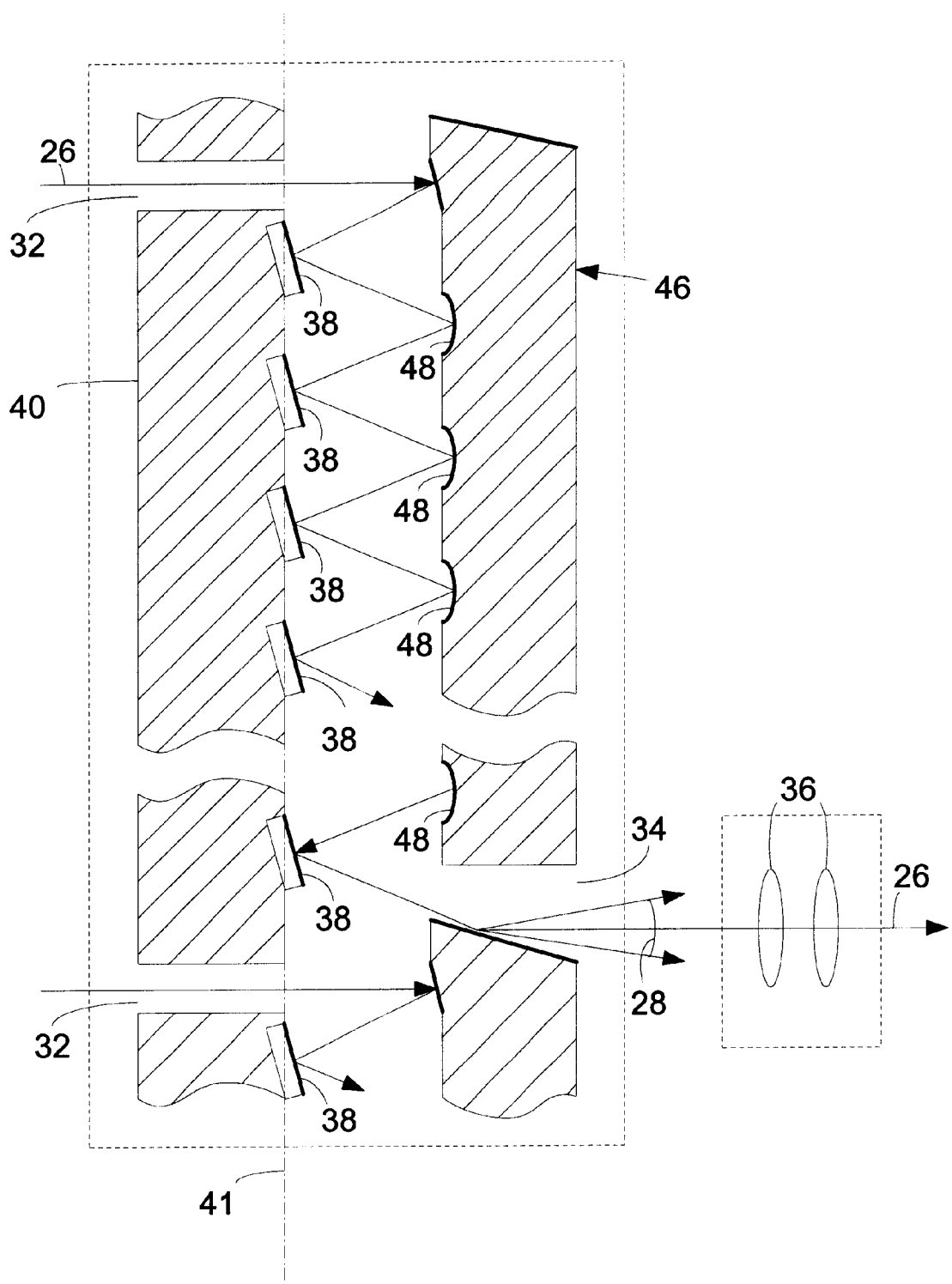
FIG. 4 illustrates the major elements of an embodiment of a single SLM.

FIG. 4 illustrates an individual SLM of the type included in arrays 10 and 12. Each SLM has an optical input 32 and an optical output 34. Output 34 is optically coupled to a pair of lenslets 36 that are in turn coupled to one of ports 24. In other embodiments of the invention, lenslets 36 can be separated, or one or both can be made an integral part of the SLM, where the SLM itself provides the optical power that lenslets 36 provide. The SLM includes a microelectromechanical structure (MEMS) and a back reflector 46. MEMS construction techniques are well-known in the art. For example, it is well-known to fabricate movable mirrors on the order of a millimeter or less in size using very large scale integration (VLSI) complementary metal-oxide semiconductor (CMOS) foundry processes. The process can include photolithography, material deposition and chemical etching. The SLM can be constructed by forming a chain of two or more microelectromechanical mirrors 38 or other reflectors upon a substrate 40 or other supporting assembly. The chain of mirrors 38 extends along a longitudinal axis or SLM axis 41 that lies in the plane of substrate 40. Substrate 40 and similar elements described below can be made, for example, of single-crystal silicon or other suitable material.

Figure 7:
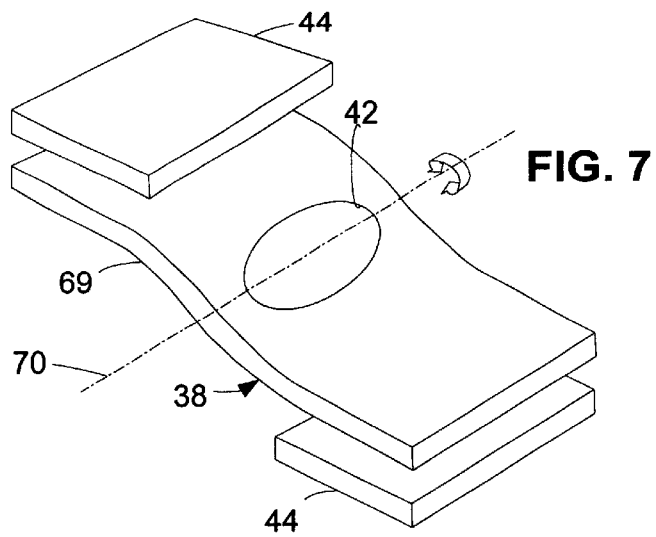
FIG. 7 is a perspective view of the major elements of an embodiment of an electrically controllable mirror of the SLM having a single axis of movement.
Figure 8:
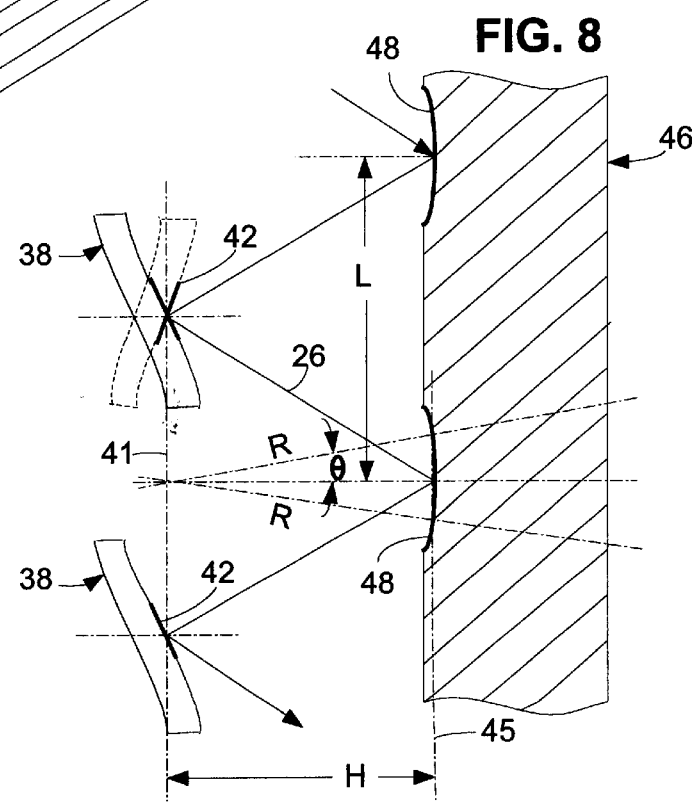
FIG. 8 is a sectional view of a portion of an SLM, enlarged to illustrate the movement of a mirror about an axis of movement.

Although the techniques for making arrays of suitable electrically actuatable MEMS mirrors 38 are well-known in the art, in the illustrated embodiment of the invention mirrors 38 have a structure of the type described in the specification of copending U.S. patent application Ser. No. 09/862,958, filed May 22, 2001, which is incorporated in its entirety into this patent specification by this reference. As illustrated in FIGS. 7 and 8, each such mirror 38 has a reflective surface portion 42 formed on a flexible membrane-like member 43. Electrodes 44 apply potentials that bias member 43 into one of two selectable switching orientations. The two orientations are illustrated in FIG. 8 in solid and dashed line. When electrodes 44 apply a potential of one polarity, mirror 38 flexes or pivots to assumes the orientation shown in solid line, and when electrodes 44 apply a potential of opposite polarity, mirror 38 flexes or pivots to assume the orientation shown in dashed line. When no potential is applied, member 43 assumes an unflexed, planar shape in which axis 41 lies in its plane. Although two switching positions are illustrated, in other embodiments of the invention each of mirrors 38 can be made to assume a selected one of any suitable number of discrete switching positions, as described in the above-referenced patent specification.

Although reflective surface portions 42 are planar or substantially planar in the illustrated embodiment of the invention, in other embodiments the reflective surfaces of such elements can be curved, either concavely or convexly, thereby contributing optical power.

Suitable alternative constructions for mirrors 38 are described in the above-referenced patent application, some of which contemplate electrostatic actuation mechanisms and others piezoelectric, magnetic and similar electrically controlled actuator technologies. Note that although other suitable electrically actuatable MEMS mirrors are known in the art, the mirror structures described in the above-referenced patent specification provide a number of advantages over prior mirror structures, including the advantage that the discrete orientations of a reflective surface 40 are extremely precisely located with respect to the overall structure to provide reliable and repeatable operation.

It should be noted that a MEMS device that performs a given function is considered in the art to be distinct from larger-scale devices that perform the same or similar function. Accordingly, as used in this patent specification, the term "MEMS" mirror 38 or "microelectromechanical" mirror 38 does not include within its scope larger, macro-scale movable mirrors or other reflectors. The present invention relates specifically to MEMS and similar micro-scale structures. For example, it is contemplated that an SLM having eight mirrors 38 can be constructed on a substrate 40 on the order of millimeters in length using known fabrication methods.

Referring again to FIG. 4, the SLM beam angle at which beam 26 emanates from output 34 (and thus port 24, which is aligned with output 34) depends upon the combined switching states of mirrors 38. Each of mirrors 38 is optically coupled to an adjacent mirror 38 through an optical pathway that, in the illustrated embodiment of the invention, includes a back reflector 46 having paraboloidal reflective surfaces 48 spaced by their focal lengths from opposing mirrors 38. Nevertheless, in other embodiments of the invention, the optical pathway coupling one mirror 38 to an adjacent mirror 38 can include any other suitable type of optical element. Beam 26 enters the SLM and is reflected by back reflector 46 onto a first one of mirrors 38. That mirror 38 reflects beam 26 onto a reflective surface 48 of back reflector 46, which, in turn, reflects beam 26 onto an adjacent mirror 38. In this manner, beam 26 propagates to successive mirrors 38 down the chain along axis 42. The last mirror in the chain reflects beam 26 onto another reflective surface 50 that directs beam 26 toward output 34.

Note that the designations "input" 32 and "output" 34 refer to the illustrated function in FIG. 4 rather than the SLM structure itself. As illustrated, the SLM can, for example, function in the input section of the switch of FIG. 1 to receive beam 26 from a fiber 20 and direct it from a port 24 at a selected beam angle to the output section of the switch. Nevertheless, the SLM can also, for example, function in the output section of the switch of FIG. 1 to receive beam 26 from a selected beam angle at a port 24 and direct it into a fiber 22. Each SLM is bidirectional. The arrows in FIG. 4 illustrating the direction of beam 26 indicate only one of the two possible directions of beam propagation through an SLM.

Returning to FIG. 8, it should be recognized that beam 26 is not a single ray but rather a nearly Gaussian beam expanding in accordance with the laws of diffraction while propagating from a reflective surface 42 of mirror 38 to a reflective surface 48 of back reflector 46. A means for refocusing beam 26, such as concave reflective surfaces 48, can be included in the invention. In this embodiment of the invention, each reflective surface 48 has a dual-paraboloidal shape that refocuses beam 26 reflected by a reflective surface 42 upon the center of a successive or adjacent reflective surface 42 regardless of the switching orientation or angle of reflective surfaces 42. Thus, focus is maintained upon the center of a successive reflective surface 42 even when a preceding reflective surface 42 changes its switching orientation. Although the means for refocusing beam 26 is a concave reflective surface 48 in this embodiment, as described below with regard to FIGS. 5 and 6, other embodiments can include other suitable means for refocusing beams 26.

The dual-paraboloidal shape of each reflective surface 48 is defined by two paraboloids adjacent one another and connected or conjoined at their vertex ends by a surface. The radius of curvature R in FIG. 8 of each of the two conjoined paraboloids, i.e., the distance from its vertex to its focus, can be expressed as $(L/2)\cos^2(\theta)/\sin(\theta)$, where L is the distance between the center of one such surface and the center of an adjacent surface, i.e., the distance between the centers of adjacent or successive reflective surfaces 48, and the angle $\theta$ is the angle between the axis normal to the center of reflective surface 48 and the radius of curvature of each of the two paraboloids. The focus of each paraboloid lies on longitudinal axis or SLM axis 41. The distance H between axis 41 and another axis 45 connecting the paraboloid vertices can be expressed as $(R/2)\cos(\theta)$. Each of the two vertices is offset along this other axis 45 from the center of reflective surface 48 by a distance of $(R/2)\sin(\theta)$. Note that the conic constant of the paraboloids is $-1$ in this example; in other embodiments other paraboloids may be suitable. In is contemplated in this embodiment that $\theta$ can be, for example, on the order of 15 degrees, and L can be on the order of a few tenths of a millimeter. It should also be noted that the above-described dual-paraboloid is only one example of a suitable concave reflector shape. Other suitable shapes, such as spherical and aspherical surfaces, will occur readily to persons skilled in the art in view of these teachings.

Figure 5:
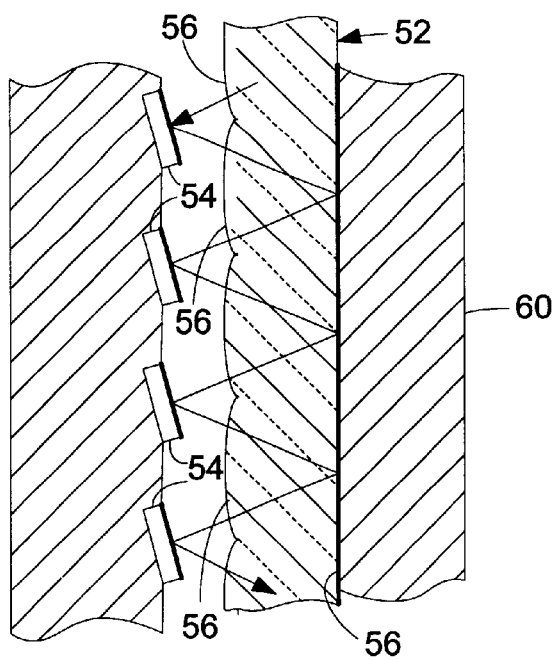
FIG. 5 illustrates a portion of an alternative embodiment of an SLM that includes an elongated refractive-medium lens.

As illustrated in FIG. 5, an alternative embodiment of an SLM can include a refractive lens medium 52 in addition to movable mirrors 54 of the same type as mirrors 38 in the above-described embodiment. Lens medium 52 extends the entire length of the SLM, between the first mirror 54 in the chain and the last. In this embodiment of the invention, the surface of lens medium 52 has lens-like convex areas 56 opposing mirrors 54 to focus beam 26 onto mirrors 54 and bring it to aperture at the reflective surface 58 of the back reflector 60 in the same manner as the dual-paraboloidal reflective surfaces 48 in the above-described embodiment.

Figure 6:
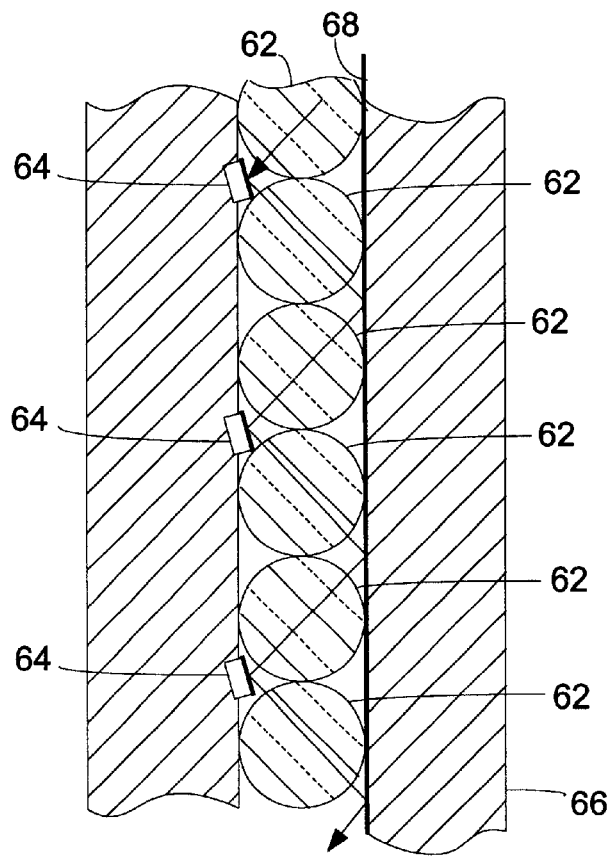
FIG. 6 illustrates a portion of another alternative embodiment of an SLM that includes spherical or ball lenses.

As illustrated in FIG. 6, another alternative embodiment of an SLM can include spherical or ball lenses 62 in addition to movable mirrors 64 of the type described above. A back reflector 66 has a reflective surface 68. In addition to focusing the beam, ball lenses 62 function as mechanical spacers between back reflector 66 and mirror substrate 70.

Figure 9:
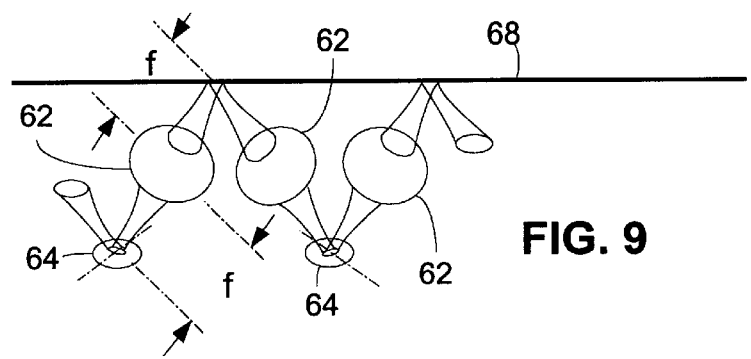
FIG. 9 illustrates the principle of a Gaussian beam propagating through spherical lenses in one embodiment of an SLM.

The focusing of a Gaussian beam by spherical or ball lenses 62 is shown in FIG. 9. Each spherical or ball lens 62 focuses beam 26 upon a reflective surface 68 of a back reflector and upon the reflective surface of a movable mirror 64. To achieve this focusing, the reflective surfaces 64 and 68 are spaced from ball lens 62 by its focal length (f). Although this focusing effect is perhaps more readily illustrated in this embodiment of the invention, the dual-parabolic reflector 48 performs a similar focusing function in the embodiment described above with regard to FIGS. 4 and 8, and refractive lens medium 52 performs a similar focusing function in the embodiment described above with regard to FIG. 5. In view of these teachings and examples, other means for performing this focusing function will occur readily to persons skilled in the art.

Note that although FIGS. 4–6 are essentially sectional views taken through the micromachined substrates, they are not to scale, and the geometries of the elements and beam 26 are shown conceptually for purposes of clarity and illustration. Persons skilled in the art to which the invention relates are familiar with MEMS movable mirror construction and the geometries necessary to produce operable SLMs of the types described in this patent specification. Such persons will appreciate that the contemplated range of motion of mirrors 38 is actually very small, perhaps only +1 degree or +2 degrees from the rest orientation in one switching orientation and $-1$ degree or $-2$ degrees from the rest orientation in the other switching orientation. (A mirror 38 is in the rest orientation when the reflective portion upon which beam 26 is focused is coplanar with that of other mirrors 38 and parallel to SLM axis 41. The rest orientation can be achieved, for example, when no mirrors 38 are actuated, i.e., in the absence of an electrical actuation signal.) Mirrors 38 can also be made to operate at speeds on the order oftens of nanoseconds. Thus, the SLMs of the present invention are well-suited for use in packet-switched optical communication networks, in which such switching speeds are desirable.

As illustrated in FIGS. 7 and 8, note that the reflective surface 42 of each mirror 38 (or at least the portion upon which beam 26 impinges) remains substantially planar even though other portions of the flexible membrane-like member 69 assume a warped or flexed shape. The plane in which reflective surface 40 lies tilts or pivots about an axis of movement 70 (FIG. 7) when the switching orientation is changed. Axis of movement 70 can be longitudinal axis 42 of the SLM, perpendicular to axis 42 as in FIGS. 4–6 and 8, or a different axis. Furthermore, the axes of movement 70 of each reflective surface 42 of each mirror 38 can be the same as that of all other mirrors 38, as in the above-described embodiments, or different mirrors can pivot about different axes.

Figure 10A:
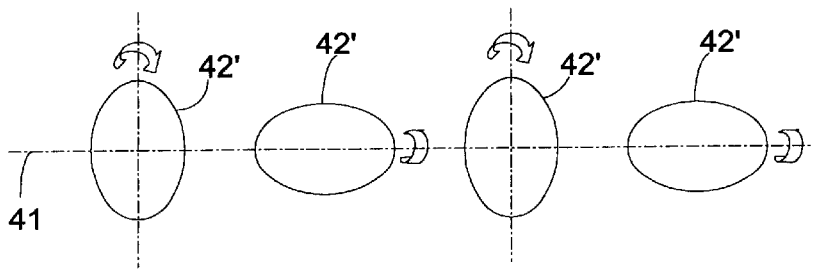
FIG. 10A illustrates an embodiment of the reflective portions of movable microelectromechanical SLM mirrors, in which each reflective portion is movable about an axis of movement perpendicular to that of the reflective portion an adjacent movable mirror.

As illustrated in FIG. 10A, in one such alternative embodiment the axes of movement of adjacent mirrors are perpendicular to one another, i.e., offset from one another by 90 degrees. In other words, adjacent mirrors (or at least the portion of their reflective surfaces 42' upon which beam 26 impinges) pivot in an alternating pitch-roll fashion, with some surfaces 42' pivoting in a pitch direction about an axis perpendicular to or offset 90 degrees from longitudinal axis 41 and other surfaces 42' pivoting in a roll direction about longitudinal axis 41 itself. Such an SLM arrangement can be used to select a beam angle from within the two-space or solid angle range 28 described above. In other words, for example, beam 26 can be directed from SLM array 10 toward a point in space and through the optical pathway such that it impinges upon a selected one of ports 24 of SLM array 12. (See FIG. 2.) By applying appropriate electrical control signals to the SLMs of array 10, beam 26 can be steered or scanned across the face of SLM array 12 that includes ports 24. It should be noted that the term "spatial light modulator" is used for convenience and is not intended to imply any particular function, characteristic, structure or number of spatial dimensions.

Figure 10B:
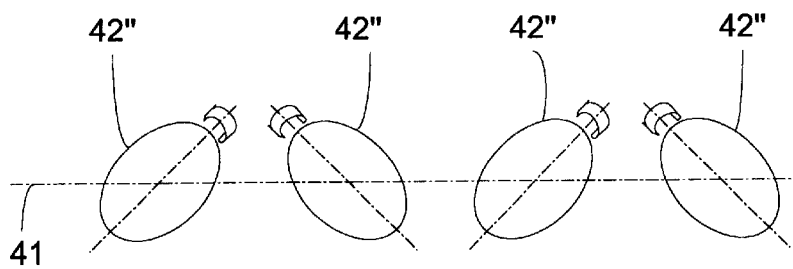
FIG. 10B illustrates an alternative embodiment of the reflective portions of SLM mirrors, in which each reflective portion is movable about an axis of movement perpendicular to and offset by 45 degrees from that of the reflective portion of an adjacent SLM mirror.
Figure 10C:
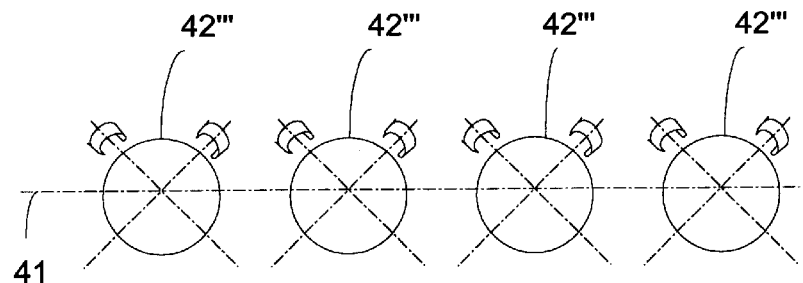
FIG. 10C illustrates another alternative embodiment of the reflective portions of SLM mirrors, in which each reflective portion is movable about two axes of movement.

As illustrated in FIGS. 10B and 10C, mirrors can pivot in other ways in still other alternative embodiments. As illustrated in FIG. 10B, the reflective surfaces 42" of some mirrors pivot about an axis of movement offset +45 degrees from longitudinal axis 41, and the reflective surfaces 42" of adjacent mirrors pivot about an axis of movement offset −45 degrees from longitudinal axis 41. Nevertheless, the offsets of +/−45 degrees in this embodiment of the invention is intended to be merely illustrative; in other embodiments the offsets can be, for example, +/−60 degrees, +/−30 degrees, +/−22.5 degrees, or any other suitable amount.

Each mirror can pivot about more than the one axis of movement 70 in the above-described embodiments. In the embodiment illustrated in FIG. 10C, each reflective surface 42''' pivots about two axes of movement offset +45 degrees and −45 degrees from longitudinal axis 41. Note that in such an embodiment each reflective surface 42''' can be oriented in one of four discrete switching orientations.

The number of discrete beam angles, i.e., directions in which beam 26 can emanate from an SLM, depends upon the number of movable mirrors per SLM and the number of axes of movement of each mirror. In the embodiment illustrated in FIG. 10A in which each reflective surface 42' pivots about a single axis of movement, the number of discrete beam angles N equals $M^2$, where M is the number of mirrors in an SLM. In the embodiment illustrated in FIG. 10C in which each reflective surface 42''' pivots about two perpendicular axes of movement, the number of discrete beam angles N equals $[4(M1)]2$, where M is the number of mirrors in an SLM. As noted above, in embodiments of the invention in which the SLM is included in a communications switch, the number of discrete beam angles N represents the number of switchable communications channels.

The equations for the number of discrete beam angles take into account that a given beam angle can in some cases be achieved by more than one combination of mirror switching orientations. To provide a set of unique beam angles, each corresponding to exactly one unique combination of switching orientations, one or more mirrors can have a switching orientation in which they are inclined at an angle different from that at which other mirrors are inclined when in that switching orientation. For example, in the single-axis of movement embodiment described above with regard to FIG. 10A, all reflective surfaces 42' except the endmost two can be inclined in one switching orientation at +X degrees from the rest position and in the other switching orientation at −X degrees from the rest position, and the endmost two can each be inclined in one switching orientation at +X/2 degrees from the rest position and in the other switching orientation at −X/2 degrees from the rest position. Thus, if all but two mirrors incline at +1 degree and −1 degree, the endmost two incline at +½ degree and −½ degree. As another example, in the two-axis of movement embodiment described above with regard to FIG. 10C, all reflective surfaces 42''' except the endmost two can be inclined in one switching orientation at +X degrees from the rest position and in the other switching orientation at −X degrees from the rest position, one of the endmost two can be inclined in one switching orientation at +X/2 degrees from the rest position and in the other switching orientation at −X/2 degrees from the rest position, and the other of the endmost two can be inclined in one switching orientation at +X/4 degrees from the rest position and in the other switching orientation at −X/4 degrees from the rest position. Thus, if all but two mirrors incline at +2 degrees and −2 degrees, one of the endmost two inclines at +1 degree and −1 degree, and the other of the endmost two inclines at +½ degree and −½ degree.

Having mirrors with differing angles of inclination as described above also facilitates selecting the beam angle because it provides, in effect, a means for making both coarse and fine angle selections. For example, changing the orientation of the endmost mirror in the embodiments described above causes the beam angle to change to one of the nearest neighboring beam angles. Thus, for example, by applying an actuation signal to the endmost mirror of an SLM of array 10 (FIG. 1), a beam can be moved from a position in which it impinges upon a port 24 of SLM array 12 to a position in which it impinges upon an adjacent port 24 of SLM array 12. In other words, the beam can be stepped across the face of SLM array 12 one port 24 at a time by actuating the fine-adjustment mirrors, i.e., the endmost mirrors. The beam can be made to skip ports 24 and move to a farther area on the face of SLM array 12 by actuating the other mirrors.

SLMs having any suitable number of discrete beam positions or channels can be achieved in view of the teachings in this patent specification. Those having 64 channels and 256 channels are specifically contemplated because such numbers of channels are common in communications routers. To achieve 64 channels with an SLM of the type indicated in FIG. 10A (i.e., each mirror having only a single axis of movement), the SLM is provided with exactly eight movable mirrors. To achieve 256 channels, this type of SLM is provided with exactly 16 movable mirrors. To achieve 64 channels with an SLM of the type indicated in FIG. 10C (i.e., each mirror having exactly two axes of movement), the SLM is provided with exactly three movable mirrors. To achieve 256 channels, this type of SLM is provided with exactly five movable mirrors. Thus, SLM embodiments consisting of exactly three, five, eight and 16 movable mirrors are of special importance. The invention is extremely scalable, and embodiments providing far more than 256 channels are believed possible. An SLM can have any suitable number of movable mirrors. It should be noted that the SLM structure of the present invention provides a greater number of channels per mirror included in the structure than in optical switching devices known in the prior art.

Note that a single SLM is itself a useful device, apart from its inclusion in a switch or other device having an array of SLMs. A single SLM can be used, for example, to receive input beams from sources at different angular positions and channel them into a single output fiber. Similarly, a single SLM can be used, for example, to receive a beam from a single fixed-position source and provide output beams at different angles.

Figure 11:
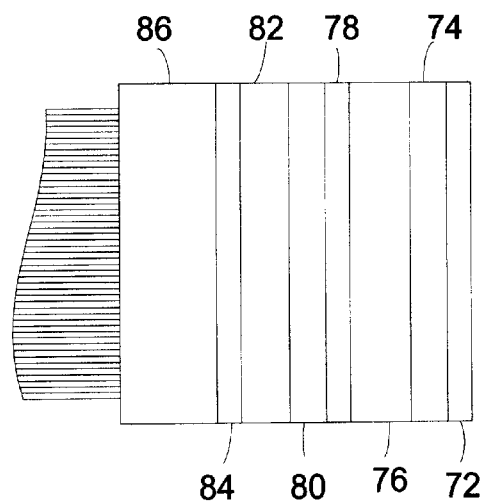
FIG. 11 is a side view conceptually illustrating the micromachined, layered construction of an SLM array.

As illustrated in FIG. 11, each of SLM arrays 10 and 12 can comprise layers defined by the MEMS substrates of the structures or elements they contain. For example, the layers can include a lenslet pair layer 72 that contains lenslets 36 (see FIG. 4); a first vacuum window layer 74; a mirror layer 76 that contains mirrors 38 and their substrate 40 (see FIG. 4); a lens layer 78 that contains lenses such as the ball or elongated types illustrated in FIGS. 5 and 6; a support layer 80 that contains a back reflector and supports the lenses; a second vacuum window layer 82; and another lenslet layer 84. Lenslet layer 84 can be connected to a fiber-accepting plate 86. The entire assembly can be enclosed in a suitable case or package (not shown). It is contemplated that the portion between vacuum windows 74 and 82 be evacuated to allow mirrors 38 to operate in a vacuum to avoid drag inhibiting mirror operation at high speeds.

Figure 12:
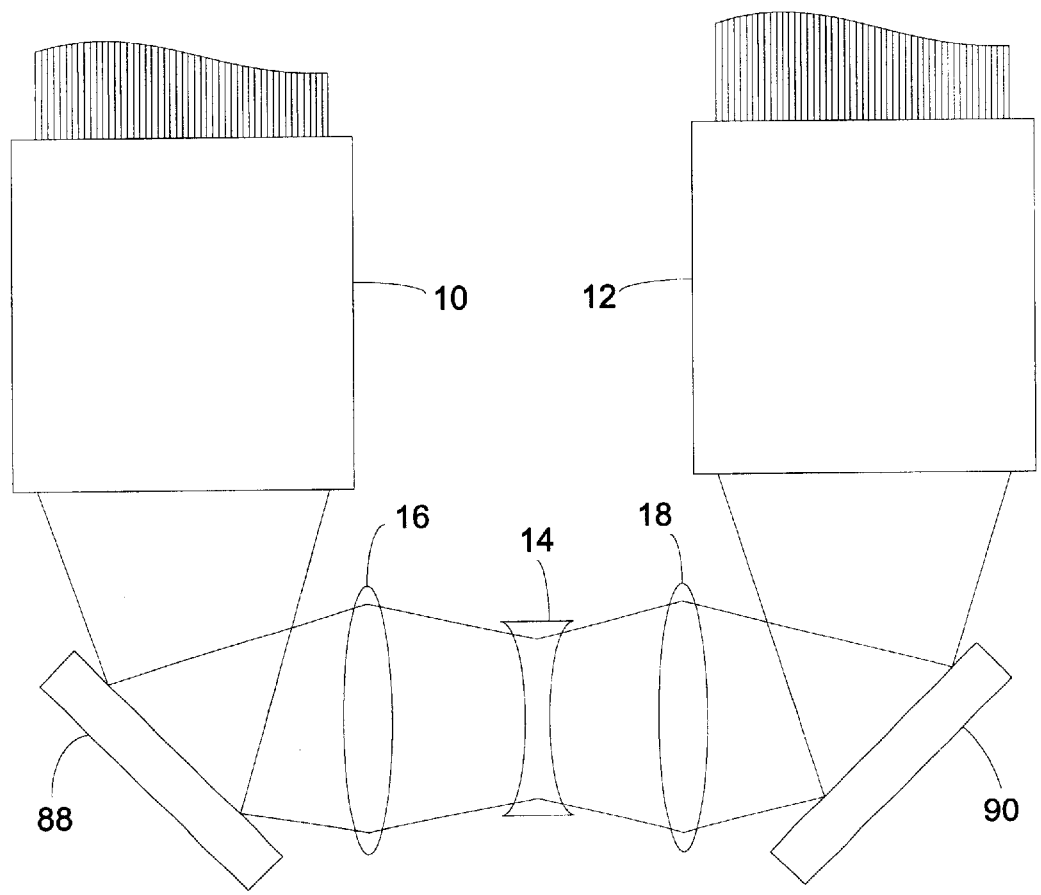
FIG. 12 is similar to FIG. 1 and illustrates an arrangement of the switch elements in which the optical path is folded into a U-shape by mirrors for compactness.

As illustrated in FIG. 12, the switch illustrated in FIG. 1 can be efficiently packaged by further including two mirrors 88 and 90 that bend or fold the optical pathway into a compact U-shape, with SLM arrays 10 and 12 at the ends of the "U." The switch can be enclosed in a suitable case or package (not shown). At scales and frequencies contemplated within the realm of this invention, the legs of the U-shape can be on the order of tens of centimeters in length, which is sufficiently compact for the entire switch to be constructed on a standard-size, rack-mounted card-cage telecommunications circuit card. Additional mirrors can be included that further bend or fold the optical pathway to further compact the overall switch structure.

Figure 13:
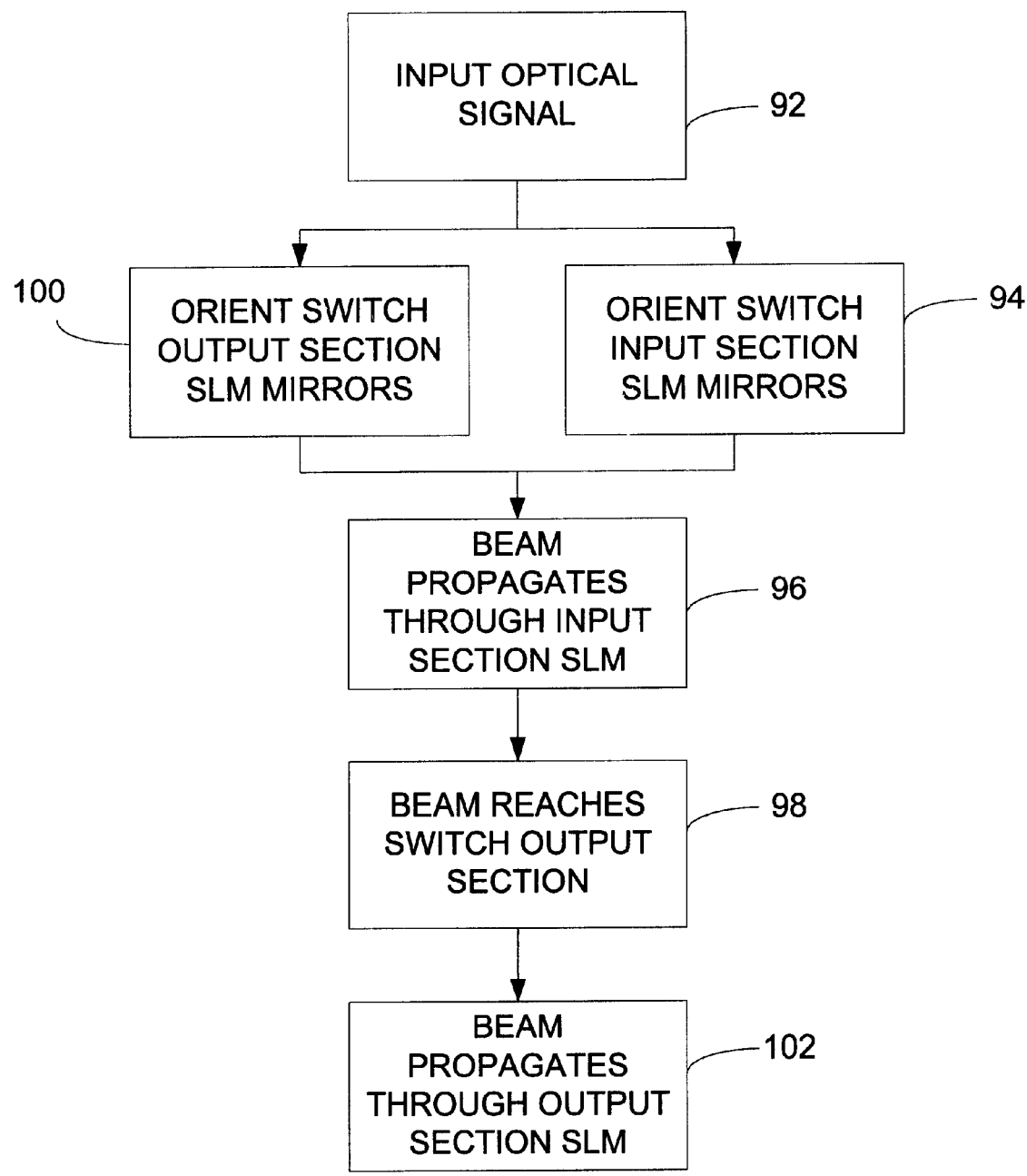
FIG. 13 is a flow diagram illustrating a switching method.

The operation of the switch can be summarized with reference to the flow diagram of FIG. 13. At step 92 an optical signal is input to one of the SLMs of the first (input) section of the switch. At step 94 the SLM mirrors are oriented in response to electrical signals such that the combination of switching orientations causes the signal to propagate from mirror to mirror down the chain and emanate from the SLM output at a corresponding beam angle. At step 96 the beam propagates through the optical pathway of lenses, mirrors or other elements to the second (output) section of the switch. In the second section of the switch, at step 98 the beam impinges upon the input of the one of the second (output) section SLMs corresponding to the selected beam angle at which the beam emanates from the first section SLM. Note that, as described above, the second section of the switch can be an array of fiber ends or similar receiving structures instead of another array of SLMs if the receiving structures have sufficient angles of acceptance. At step 100 the mirrors of that second section SLM are oriented in response to electrical signals such that the combination of switching orientations causes the signal to be received at the second section SLM input and propagate at step 102 from mirror to mirror down the chain and emanate from the second section SLM output. The first section SLMs can be included in SLM array 10, and the signal input to the switch can be a selected one of fibers 20. The second section SLMs can be included in SLM array 12, and the signal output from the switch can be a selected one of fibers 22. (See FIG. 1.) By applying the appropriate control signals, an optical signal from any selected one of fibers 20 can be coupled to any selected one of fibers 22 (which can be single-mode fibers) in a cross-connect or crossbar manner.

It will be apparent to those skilled in the art that various modifications and variations can be made in the present invention without departing from the scope or spirit of the invention. Other embodiments of the invention will be apparent to those skilled in the art as a result of consideration of the specification and practice of the invention disclosed herein. It is intended that the specification and examples be considered as exemplary only, with the true scope and spirit of the invention being indicated by the following claims.

What is claimed is:

1. A spatial light modulator (SLM) for directing an optical signal, comprising:
   an optical input;
   a reflector assembly comprising a plurality of electrically controllable microelectromechanical movable reflectors disposed along an SLM axis, each movable reflector having a reflective surface electrically pivotable in a selectable one of a plurality of discrete switching orientations, a first movable reflector of the plurality of movable reflectors optically coupled to the optical input to receive an optical signal from the optical input, each successive movable reflector of the plurality of movable reflectors optically coupled to a preceding movable reflector of the plurality of movable reflectors to receive the optical signal reflected by the preceding movable reflector, a last movable reflector of the plurality of movable reflectors optically coupled to a preceding movable reflector to receive the optical signal reflected by the preceding movable reflector; and
   an optical output optically coupled to the last movable reflector to receive the signal reflected by the last movable reflector.

2. The SLM claimed in claim 1, wherein the optical output is coupled to a single-mode fiber.

3. The SLM claimed in claim 1, wherein the optical input is coupled to a single-mode fiber.

4. The SLM claimed in claim 1, wherein the optical input is coupled to a laser source.

5. The SLM claimed in claim 1, wherein the plurality of movable reflectors is at least three.

6. The SLM claimed in claim 1, wherein the reflective surface of each movable reflector is substantially planar in a plane pivotable about a movement axis lying substantially in the plane.

7. The SLM claimed in claim 6, wherein each movable reflector has a reflective surface electrically orientable in a selectable one of exactly two discrete switching orientations.

8. The SLM claimed in claim 7, wherein the plurality of movable reflectors consists of exactly eight.

9. The SLM claimed in claim 7, wherein the plurality of movable reflectors consists of exactly sixteen.

10. The SLM claimed in claim 6, wherein each movable reflector has a reflective surface electrically orientable in a selectable one of exactly four discrete switching orientations.

11. The SLM claimed in claim 10, wherein the plurality of movable reflectors consists of exactly three.

12. The SLM claimed in claim 10, wherein the plurality of movable reflectors consists of exactly five.

13. The SLM claimed in claim 1, wherein the two switching orientations of a reflective surface of each reflector of the plurality of movable reflectors are the same as the two switching orientations of the reflective surfaces of all other movable reflectors of the plurality of movable reflectors.

14. The SLM claimed in claim 1, wherein:
   the plurality of movable reflectors consists of a first group of reflectors and a second group of reflectors;
   the reflective surfaces of the first group of reflectors are pivotable about a first movement axis; and
   the reflective surfaces of the second group of reflectors are pivotable about a second movement axis different from the first movement axis.

15. The SLM claimed in claim 14, wherein reflectors of the first group and reflectors of the second group are disposed alternately along the SLM axis.

16. The SLM claimed in claim 15, wherein the second movement axis is offset 90 degrees from or perpendicular to the first movement axis.

17. The SLM claimed in claim 16, wherein the first movement axis is the SLM axis.

18. The SLM claimed in claim 15, wherein the first movement axis is offset 45 degrees from the SLM axis.

19. The SLM claimed in claim 18, wherein the reflective surface of each movable reflector is pivotable about first and second movement axes offset 90 degrees or perpendicular to each other.

20. The SLM claimed in claim 1, wherein the reflective surface of each movable reflector is disposed on a flexible membrane.

21. The SLM claimed in claim 1, wherein the reflector assembly includes a back reflector having at least one reflective surface opposing and between the reflective surfaces of adjacent movable reflectors, and the reflective surface of the back reflector is optically coupled to the reflective surface of each of two adjacent movable reflectors to receive the optical signal reflected by one of the two adjacent movable reflectors and reflect the optical signal onto the other of the two adjacent movable reflectors.

22. The SLM claimed in claim 21, wherein the back reflector includes a substrate having disposed thereon a reflective surface extending along the apparatus axis from the first movable reflector to the last movable reflector.

23. The SLM claimed in claim 21, further comprising a lens structure interposed between a reflective surface of a movable reflector and a reflective surface of the back reflector.

24. The SLM claimed in claim 23, wherein the lens structure comprises a ball lens.

25. The SLM claimed in claim 24, wherein a ball lens is interposed between the reflective surface of each movable reflector of the plurality of movable reflectors and a reflective surface of the back reflector.

26. The SLM claimed in claim 23, wherein the lens structure comprises a refractive medium extending along the apparatus axis from the first movable reflector to the last movable reflector.

27. The SLM claimed in claim 26, wherein the refractive medium has a curved lens-shaped portion between the reflective surface of each movable reflector of the plurality of movable reflectors and a reflective surface of the back reflector.

28. The SLM claimed in claim 1, wherein:
each of the plurality of movable reflectors has a rest position in which its reflective surface is coplanar with the reflective surface of all other movable reflectors of the plurality of movable reflectors and parallel to the SLM axis; and
the discrete switching orientations are at discrete angular deviations from the rest position; and
the discrete switching orientations of at least one reflective surface of a movable reflector are at angular deviations different from the angular deviations of at least one other reflective surface of a movable reflector.

29. The SLM claimed in claim 28, wherein the discrete switching orientation of the at least one reflective surface of a movable reflector is at an angular deviation one-half the angular deviation of a plurality of other reflective surfaces of movable reflectors.

30. The SLM claimed in claim 29, wherein the discrete switching orientation of the at least one reflective surface of a movable reflector is at an angular deviation one-fourth the angular deviation of a plurality of other reflective surfaces of movable reflectors.

31. The SLM claimed in claim 28, wherein the discrete switching orientation of none of the reflective surfaces of the movable reflectors is at an angular deviation exceeding two degrees.

32. A spatial light modulator (SLM) array for directing an optical signal, comprising:
a micromachined supporting assembly;
a plurality of first optical ports arranged in the supporting assembly;
a plurality of SLM reflector assemblies, each SLM reflector assembly comprising one or more electrically controllable microelectromechanical movable reflectors arranged along an SLM axis, each movable reflector having a reflective surface electrically pivotable in a selectable one of a plurality of discrete switching orientations, a first movable reflector optically coupled to one of the first optical ports to receive an optical signal from the one of the first optical ports, a last movable reflector optically coupled to a preceding movable reflector to receive the optical signal reflected by the preceding movable reflector; and
a plurality of second optical ports in the supporting assembly, each second optical port optically coupled to the last movable reflector of one of the SLM reflector assemblies to receive the optical signal.

33. The SLM array claimed in claim 32, wherein each SLM reflector assembly comprises a plurality of the movable reflectors.

34. The SLM array claimed in claim 33, wherein:
the plurality of first optical ports are disposed in a two-dimensional arrangement in the supporting assembly; and
the plurality of second optical ports are disposed in a two-dimensional arrangement in the supporting assembly.

35. The SLM array claimed in claim 34, wherein each first optical port is couplable to an optical fiber to receive the optical signal from the optical fiber.

36. The SLM array claimed in claim 34, wherein each second optical port is couplable to an optical fiber to provide the optical signal to the optical fiber.

37. The SLM array claimed in claim 34, wherein the plurality of first optical ports are arranged in a rectangular array in the supporting assembly.

38. The SLM array claimed in claim 34, wherein the plurality of second optical ports are arranged in a rectangular array in the supporting assembly.

39. A method for directing an optical signal, comprising:
inputting an optical signal at an optical input;
pivoting each of a plurality of microelectromechanical movable reflectors arranged along an axis into one of a plurality of discrete switching orientations in response to electrical switching signals;
propagating the optical signal impinging upon one of the movable reflectors to a successive one of the movable reflectors; and
outputting the optical signal reflected from the successive one of the movable reflectors at an optical output.

40. The method claimed in claim 39, wherein the inputting step comprises receiving the optical signal from an optical fiber.

41. The method claimed in claim 39, wherein the inputting step comprises receiving the optical signal from a laser source.

42. The method claimed in claim 39, wherein the outputting step comprises providing the optical signal at a non-zero angle with respect to the axis, and the angle is determined in response to the discrete switching orientations of the movable reflectors via which the optical signal propagates.

43. The method claimed in claim 39, wherein the outputting step comprises providing the optical signal to an optical fiber.

44. The method claimed in claim 43, wherein the outputting step comprises providing the optical signal to an photodetector.

45. The method claimed in claim 39, wherein the orienting step comprises orienting a movable reflector to receive the optical signal at a non-zero angle with respect to the axis and optically couple the optical signal to an adjacent movable reflector.

46. The method claimed in claim 39, wherein the propagating step comprises:
   the one of the movable reflectors reflecting the optical signal onto a back reflector; and
   the back reflector reflecting the optical signal onto the successive one of the movable reflectors.

47. The method claimed in claim 39, wherein the orienting step comprises pivoting a reflective portion of each movable reflector about a movement axis.

48. The method claimed in claim 47, wherein the orienting step comprises:
   pivoting a reflective portion of a first movable reflector about a first movement axis; and
   pivoting a reflective portion of a second movable reflector about a second movement axis different from the first movement axis.

* * * * *